(12) United States Patent
Cardon et al.

(10) Patent No.: US 11,013,619 B2
(45) Date of Patent: May 25, 2021

(54) INSTRUMENTATION AND METHOD FOR IMPLANTING A GLENOIDAL PROSTHETIC COMPONENT ON A GLENOID

(71) Applicant: Tornier, Montbonnot-Saint-Martin (FR)

(72) Inventors: Jean-Emmanuel Cardon, Domene (FR); Lionel Neyton, Genas (FR)

(73) Assignee: TORNIER, Montbonnot-Saint-Martin (FR)

( * ) Notice: Subject to any disclaimer, the term of this patent is extended or adjusted under 35 U.S.C. 154(b) by 0 days.

(21) Appl. No.: 15/451,163

(22) Filed: Mar. 6, 2017

(65) Prior Publication Data
US 2017/0273806 A1     Sep. 28, 2017

(30) Foreign Application Priority Data

Mar. 22, 2016 (FR) ...................... 1652448

(51) Int. Cl.
*A61F 2/40* (2006.01)
*A61B 17/56* (2006.01)
(Continued)

(52) U.S. Cl.
CPC .......... *A61F 2/4657* (2013.01); *A61F 2/4081* (2013.01); *A61F 2/46* (2013.01);
(Continued)

(58) Field of Classification Search
CPC ................ A61B 34/20; A61B 17/1778; A61B 2017/0414; A61B 17/1684;
(Continued)

(56) References Cited

U.S. PATENT DOCUMENTS 4,305,394 A * 12/1981 Bertuch, Jr. .............. A61F 2/34
606/91
7,335,207 B1 * 2/2008 Smith ................... A61F 2/4609
606/99
(Continued)

FOREIGN PATENT DOCUMENTS

EP     1 332 734     8/2003
EP     1 457 159     9/2004

OTHER PUBLICATIONS

Search Report issued in French Application No. 1652448, dated Jan. 19, 2017, in 2 pages.
(Continued)

*Primary Examiner* — Ann Schillinger
(74) *Attorney, Agent, or Firm* — Duane Morris LLP

(57) ABSTRACT

An instrument used for the implantation of a glenoidal prosthetic component is disclosed. A relative position of a glenoidal prosthesis component and of a plate is adjustable around an implantation axis before fixing the assembly. The instrument comprises a tool for positioning the glenoidal prosthetic component and the plate relatively to each other angularly around the implantation axis. The instrument includes a tool that has a body, which, in use, extends transversely to the implantation axis and which is provided with localization elements for localizing an implantation angle centered on the implantation axis, so that the tool is able to intra-operatively protract the implantation angle with respect to the glenoid.

8 Claims, 8 Drawing Sheets

(51) Int. Cl.
*A61F 2/46* (2006.01)
*A61F 2/30* (2006.01)

(52) U.S. Cl.
CPC ..... *A61F 2/4603* (2013.01); *A61F 2002/3054* (2013.01); *A61F 2002/30332* (2013.01); *A61F 2002/30507* (2013.01); *A61F 2002/30617* (2013.01); *A61F 2002/30878* (2013.01); *A61F 2002/30901* (2013.01); *A61F 2002/4085* (2013.01); *A61F 2002/4668* (2013.01)

(58) Field of Classification Search
CPC .......... A61B 17/1703; A61B 2017/568; A61B 17/1739; A61B 17/0483; A61B 17/1666; A61B 17/15; A61F 2/4081; A61F 2/4612; A61F 2002/30332; A61F 2/0811; A61F 2002/30433; A61F 2/4684; A61F 2/0805; A61F 2002/4022; A61F 2/4657; A61F 2/30749; A61F 2/30771; A61F 2/4637; A61F 2002/305; A61F 2002/30772; A61F 2002/3084
See application file for complete search history.

(56) References Cited

U.S. PATENT DOCUMENTS

| | | |
|---|---|---|
| 2004/0230197 A1* | 11/2004 | Tornier .............. A61B 17/1778 606/87 |
| 2009/0270993 A1 | 10/2009 | Maisonneuve et al. |
| 2011/0224674 A1* | 9/2011 | White ................... A61F 2/4609 606/91 |
| 2013/0267958 A1 | 10/2013 | Iannotti et al. |
| 2014/0107654 A1 | 4/2014 | Kehres et al. |
| 2014/0257304 A1 | 9/2014 | Eash |
| 2015/0157462 A1 | 6/2015 | Ek et al. |

OTHER PUBLICATIONS

Extended European Search Report in Application No. 17161950.5, dated Apr. 13, 2017 in 7 pages.

* cited by examiner

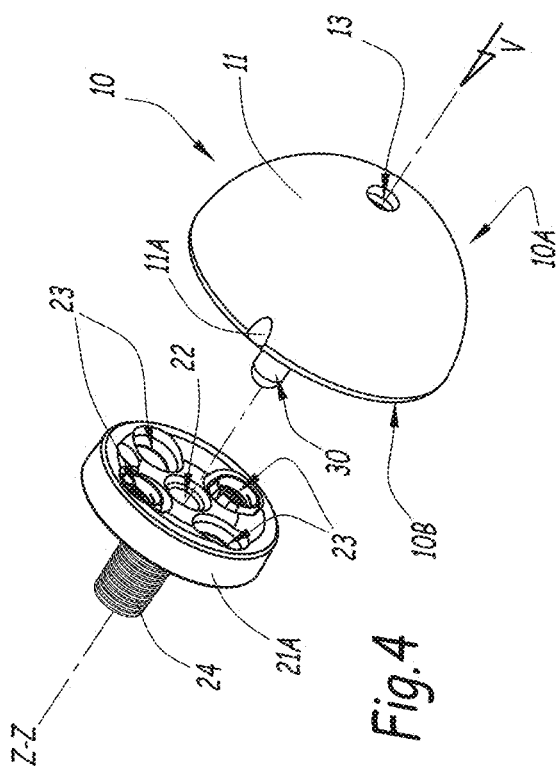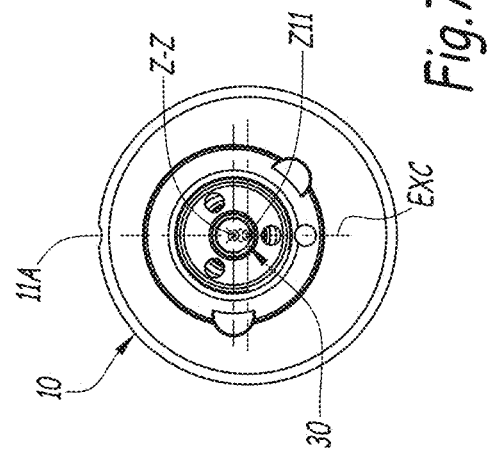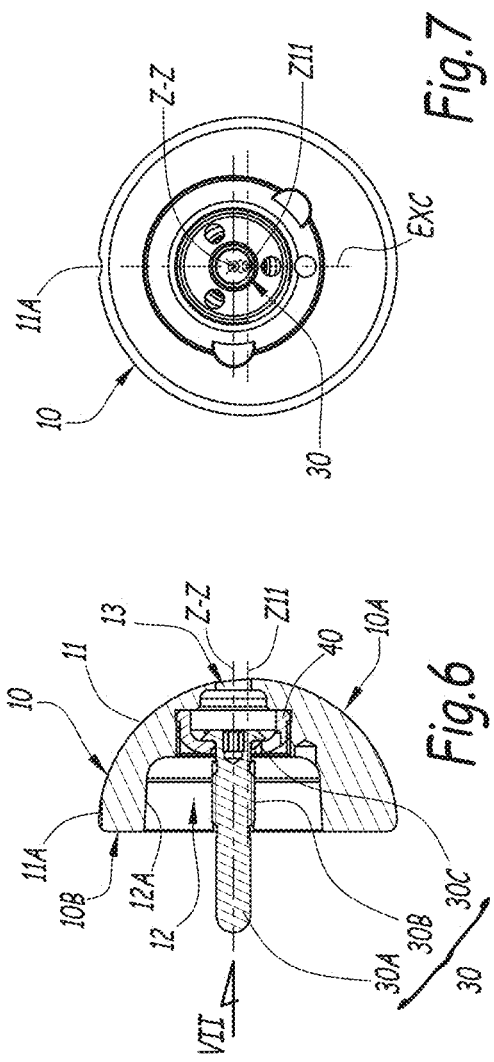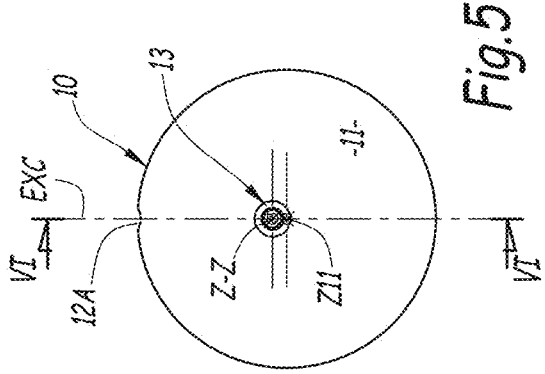

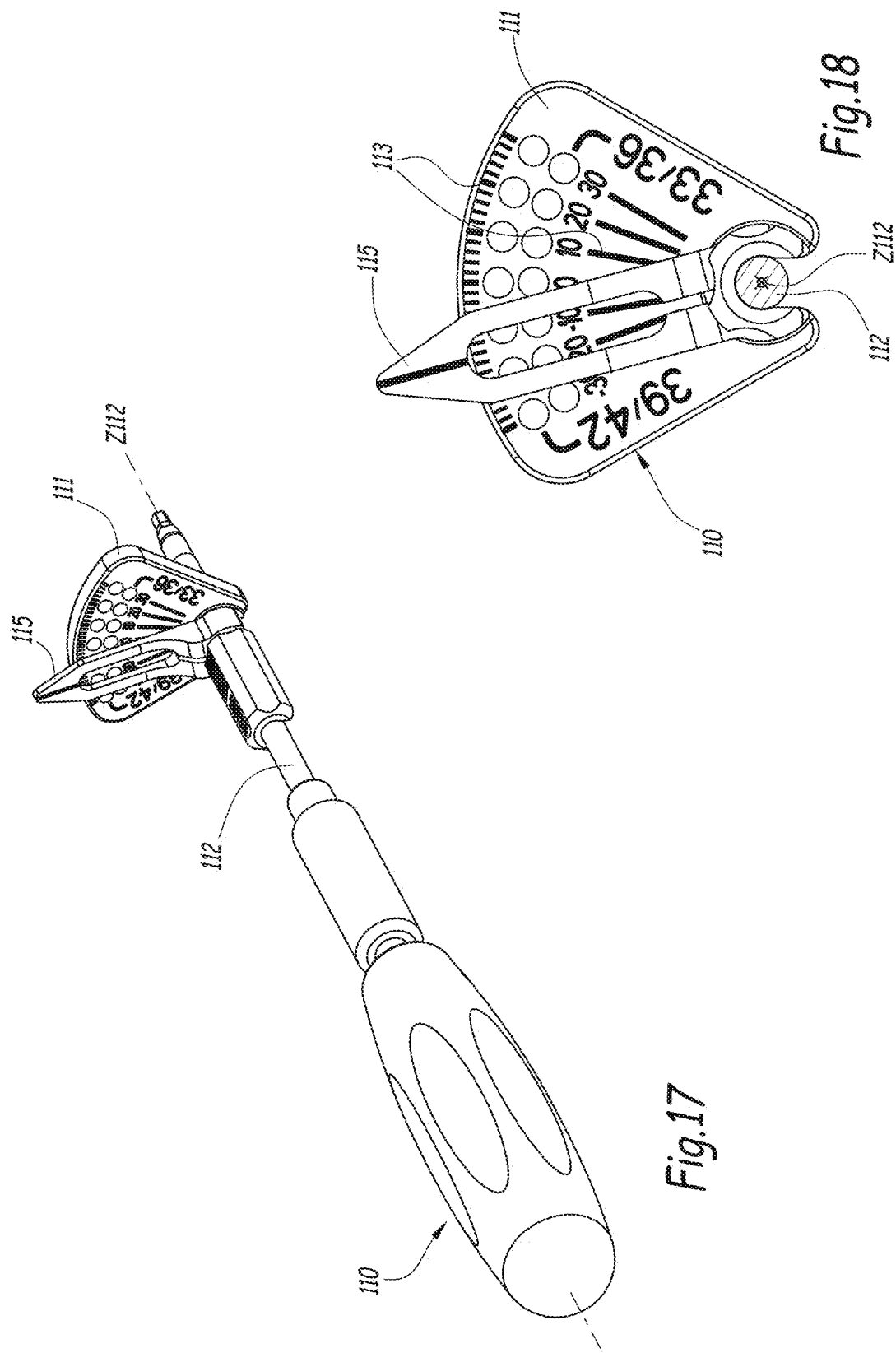

INSTRUMENTATION AND METHOD FOR IMPLANTING A GLENOIDAL PROSTHETIC COMPONENT ON A GLENOID

CROSS-REFERENCES TO RELATED APPLICATIONS

This application claims priority to Application No. FR 1652448, filed on Mar. 22, 2016.

BACKGROUND OF THE INVENTION

Field of the Invention

The present invention relates to instrumentation for implanting a glenoidal prosthesis component onto a glenoid of a patient. It also relates to a kit for surgical treatment of a glenoid of a patient. It also relates to a method for implanting a glenoidal prosthesis component on a glenoid of a patient.

Description of the Related Art

In the field of arthroplasty of the shoulder, it is known how to implant a so called reversed shoulder prosthesis, which as opposed to the anatomic articular structure of the shoulder, comprises a glenoidal prosthesis component, having a convex articular surface, and a humeral prosthetic component having a concave articular surface, against which is articulated the articular surface of the glenoidal prosthetic component. Generally, the glenoidal prosthesis component is called a glenosphere. In order to attach this glenosphere to the glenoid, the glenoid is milled beforehand and a mounting plate is placed on the glenoid and then is anchored to the glenoid. The plate is then fixedly assembled to the glenosphere by being received at least partly inside the latter, more specifically in a housing of the glenosphere which is provided as a recess in the face of the glenosphere, opposite to its convex articular surface.

Such a reversed shoulder prosthesis leads to medializing and to lowering the joint interface between the glenosphere and the humeral prosthetic component, in particular the centre of rotation of the shoulder fitted with a prosthesis, which allows an increase in the lever arm of the deltoid. This prosthesis is therefore particularly indicated when the cuff of the patient is strongly damaged, or even partly or totally torn.

SUMMARY OF THE INVENTION

This being the case, with this type of reversed shoulder prosthesis, it is frequent during an adduction movement of the shoulder, that the lower portion of the humeral prosthetic component will hit the pillar of the scapula, i.e. the lower portion of the scapula, laid out under the glenoid and located just below the glenosphere. This interference between the humeral prosthetic component and the scapula, the occurrence of which depends on the anatomy of the patient, limits the amplitude of the adduction movement and may induce pain for the patient, or even lead finally to detachment of the prosthesis. Also, for limiting the occurrence of this interference, it is known how to off-center the glenosphere relatively to the plate: the joint axis, which defines the convex articular surface of the glenosphere, is no longer aligned with the implantation axis along which this glenosphere is attached to the plate, but is shifted downwards relatively to this implantation axis. In practice, for such an eccentric glenosphere, the central axis of the housing of the latter is shifted upwards relatively to the joint axis, this central axis will align with the implantation axis in the assembled condition of the glenosphere with the plate. When an eccentric glenosphere is used, the surgeon is required to make sure that the offset between the glenosphere and the plate is maximum in the direction substantially vertical passing through the upper anatomic point and the lowest anatomic point of the glenoid of the patient: in this way, it is sought to offset as much as possible the glenosphere relatively to the glenoid. To do this, provision is made so that the assembling between the glenosphere and the plate allows, before fixing of this assembly, adjustment of the relative position of the glenosphere and of the plate around the implantation axis, typically by driving the glenosphere into rotation around the implantation axis relatively to the plate already anchored in the glenoid.

The object of the present invention is to improve the implantation of an reversed shoulder prosthesis with an eccentric glenosphere.

For this purpose, one object of the invention is an instrumentation for implanting a glenoidal prosthesis component on a glenoid of a patient, this glenoidal prosthetic component being provided with a convex articular surface which defines a joint axis and which is intended to articulate with a humeral prosthetic component. This glenoidal prosthetic component is also adapted to be fixedly assembled with a plate to be anchored to the glenoid, an assembly between the glenoidal prosthetic component and the plate being centered on an implantation axis which is both parallel and shifted with respect to the joint axis, the relative position of the glenoidal prosthetic component and of the plate being adjustable around the implantation axis before fixing the assembly. The instrumentation comprises a tool for positioning the glenoidal prosthetic component and the plate relatively to each other, angularly around the implantation axis, this tool comprising a body, which, in use, extends transversely to the implantation axis and which is provided with localization elements for localizing an implantation angle centered on the implantation axis, so that the tool is able to intra-operatively protract the implantation angle with respect to the glenoid.

Another object of the invention is also a kit for surgical treatment of a glenoid of a patient, including:
  a plate adapted to be anchored to the glenoid,
  a glenoidal prosthetic component, which is provided with a convex articular surface, defining a joint axis and intended to articulate with a humeral prosthetic component, and which is adapted to be fixedly assembled with the plate by an assembly being centered on an implantation axis which is both parallel and shifted relatively to the joint axis, the relative position of the glenoidal prosthetic component and of the plate being adjustable around the implantation axis before fixing this assembly, and
  an instrumentation for implanting the glenoidal prosthetic component on the glenoid, the instrumentation comprising a tool for positioning the glenoidal prosthetic component and the plate relatively to each other, angularly around the implantation axis, this tool comprising a body, which, in use, extends transversely to the implantation axis and which is provided with localization elements for localizing an implantation angle centered on the implantation axis, so that the tool is able to intra-operatively protract the implantation angle with respect to the glenoid.

Another object of the invention is also a method for implanting a glenoidal prosthetic component on a glenoid of a patient, this glenoidal prosthetic component being provided with a convex articular surface which defines a joint axis and which is intended to articulate with a humeral prosthetic component, this glenoidal prosthetic component being also adapted to be fixedly assembled with a plate to be anchored to the glenoid, an assembly between the glenoidal prosthetic component and the plate being centered on an implantation axis which is both parallel and shifted relatively to the joint axis, the relative position of the glenoidal prosthetic component and of the plate being adjustable around the implantation axis before fixing of the assembly, which method comprises:

- a preoperative phase, during which, from preoperative data, an implantation angle is determined with which the glenoidal prosthetic component is to be positioned around the implantation axis relatively to the glenoid so that, when projected into a plane perpendicular to the implantation axis, an eccentricity line passing through the implantation axis and the joint axis avoids the pillar of the scapula of the patient, and
- an intra-operative phase, during which the implantation angle is protracted with respect to the glenoid and, after having assembled the glenoidal prosthetic component with the plate anchored beforehand to the glenoid, the assembly is fixed by observing the implantation angle.

One of the ideas of the basis of the invention lies on the observation that, depending on the patients, the pillar of the scapula is not systematically positioned in the alignment of the substantially vertical direction passing through the uppermost and lowest anatomic points of the glenoid of the patient. On the contrary, it is ascertained that the pillar of the scapula is often positioned rearwards of this direction. As the eccentric assembly between the glenoidal prosthetic component and the plate allows, before fixing this assembly, adjustment of the relative position of the glenoidal prosthetic component and of the plate around the implantation axis, the invention provides, by means of an ad hoc tool, protracting onto the glenoid an implantation angle centered on the implantation axis, allowing angular positioning of the glenoidal prosthetic component relatively to the plate by taking into account the effective position of the pillar of the scapula. In particular, this implantation angle is provided so that, in projection in a plane perpendicular to the implantation axis, the eccentricity line, passing through the implantation axis and the joint axis, avoids the pillar of the scapula. The invention thus allows, easily and rapidly, optimization of the implantation positioning of the eccentric glenoidal prosthetic component of a reversed shoulder prosthesis, in other words optimization of the implantation of an eccentric glenosphere, and this without requiring new or particular arrangements of this glenosphere.

According to advantageous features of the instrumentation and/or of the kit according to the invention:

The localization elements comprise angular graduations which are centered on the implantation axis.

The tool further comprises a rod which, in use, is centered on the implantation axis and which bears the body.

The rod is provided with an end part which is adapted for cooperating with the plate so as to center the rod on the implantation axis.

The end part of the rod is adapted for cooperating by shape matching with the plate so as to center the rod on the implantation axis.

The tool further comprises a sight which is movable with respect to the body so as to individually aim at each of the localization elements.

The instrumentation further comprises at least one pin able to be attached to the glenoid, and the tool is adapted for guiding and setting into place said at least one pin on the glenoid so that said at least one pin localizes the implantation angle.

The body is provided with through-orifices which are associated with at least some of the localization elements and which are each adapted for receiving in a complementary way said at least one pin so as to guide and set into place said at least one pin on the glenoid.

The articular surface of the glenoidal prosthetic component is provided with a notch which, when projected into a plane perpendicular to the implantation axis, is aligned with an eccentricity line passing through the implantation axis and the joint axis.

Also, according to advantageous features of the method according to the invention:

the preoperative data are issued from scanner and/or radiological images of the scapula of the patient;

during the preoperative phase, the implantation angle is determined by measuring, when projected into the plane perpendicular to the implantation axis, a geometrical angle formed between the eccentricity line and a reference line which passes through the implantation axis and an anatomic mark of the glenoid, such as the apex of the glenoid;

during the intra-operative phase, the implantation angle is protracted relatively the glenoid by using a tool which after having been centered on the implantation axis and positioned relatively to an anatomic mark of the glenoid, such as the apex of the glenoid, allows construction of the implantation angle relatively to this anatomic mark;

during the intra-operative phase, the tool is used after the plate has been anchored to the glenoid and is centered on the implantation axis by cooperating with the plate;

the tool comprises a body, which, in use, extends transversely to the implantation axis and which is provided with localization elements for localizing the implantation angle.

BRIEF DESCRIPTION OF THE DRAWINGS

The invention will be better understood upon reading the description which follows, only given as an example and made with reference to the drawings wherein:

FIG. 4 is a perspective view of a glenoidal prosthetic set;

FIG. 5 is an elevational view, along the arrow V of FIG. 4, of a component belonging to the set of FIG. 4;

FIG. 6 is a sectional view along the line VI-VI of FIG. 5;

FIG. 7 is an elevational view along the arrow VII of FIG. 6;

FIGS. 17 and 18 are views respectively similar to FIGS. 1 and 3 and illustrate an optional arrangement of the instrumentation according to the invention.

DETAILED DESCRIPTION

Figure 1:
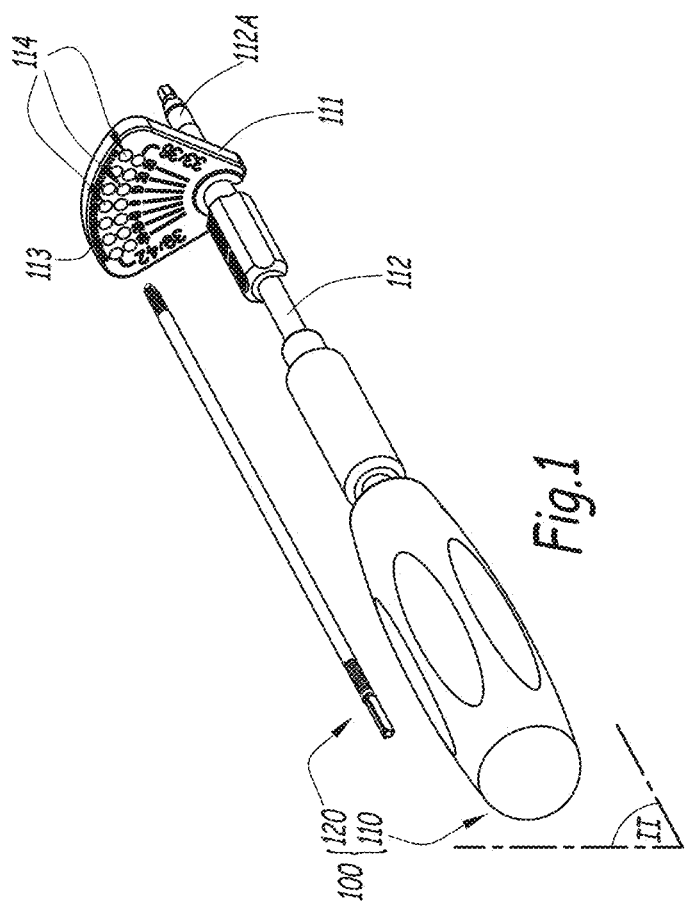
FIG. 1 is a perspective view of instrumentation according to the invention.

In FIG. 1, is illustrated a surgical instrumentation 100.

Figure 3:
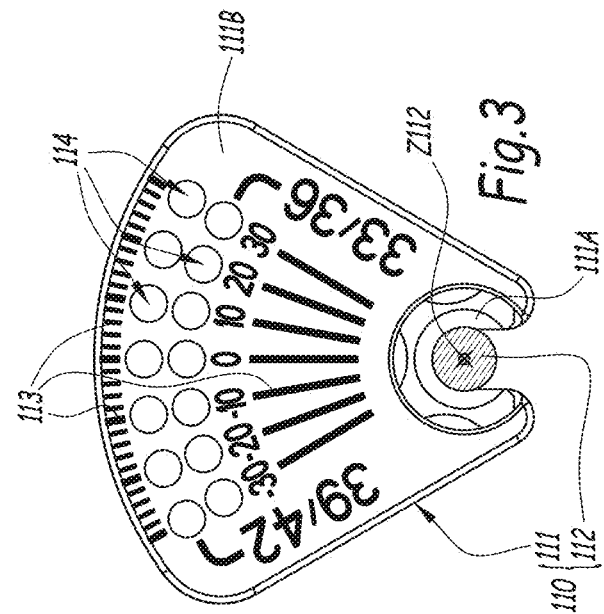
FIG. 3 is a sectional view along the line III-III of FIG. 2.
Figure 2:
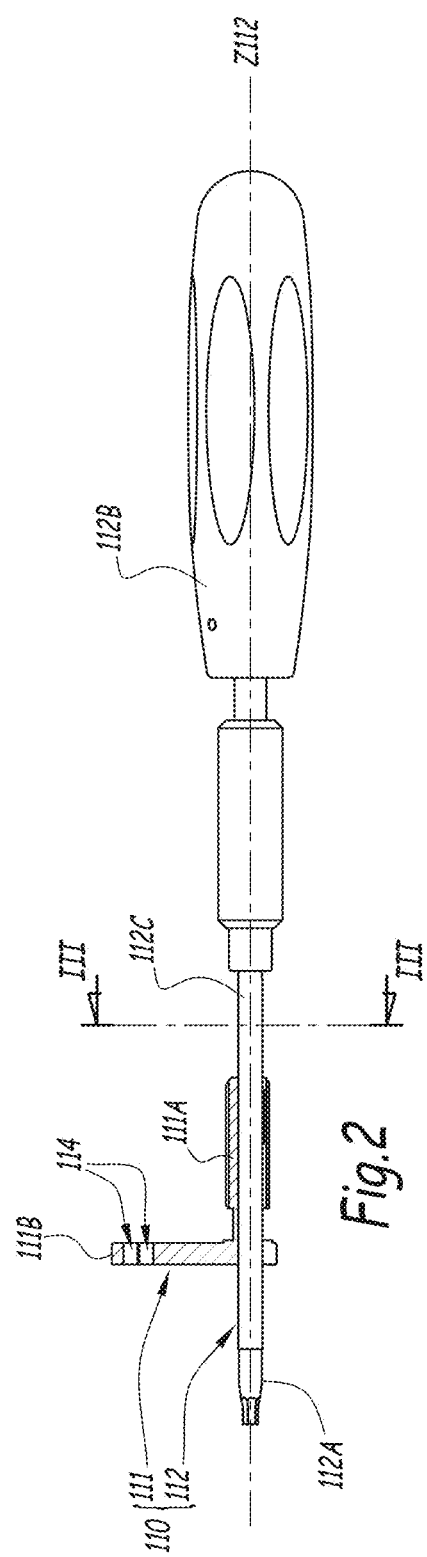
FIG. 2 is a sectional view, along the plane II of FIG. 1, of a tool belonging to the instrumentation of FIG. 1.

This instrumentation 100 comprises a tool 110 which is shown alone in FIGS. 2 and 3. This tool 110 mainly includes a body 111 and a rod 112, which are globally arranged in a transversal way relatively to each other.

More specifically, the rod 112 is centered on a geometrical axis Z112 along which the rod 112 extends in length. The rod 112 has:
- a distal terminal portion 112A, which is free,
- a proximal terminal portion, which is securely provided with a gripping handle 112B, and
- a running portion 112C, which connects the distal terminal portion 112A and the handle 112B to each other, and which bears the body 111.

The portion of the body 111, turned towards the running portion 112C of the rod 112, forms a gun 111A which, by wrapping the running portion 112C of rod 112, gives the possibility of assembling the body 111 to the rod 112, by attaching them together while allowing, if necessary, an adjustment of their respective angular position around the axis Z112. The remainder of the body 111 forms a plate 111B which, in the assembled condition of the tool 110, extends from the running portion 112C of the rod 112 in a transversal way or even perpendicularly to the axis Z112. According to an optional advantageous positioning, this plate 111B is made in a transparent material.

On its proximal face, i.e. on its face turned towards the gripping handle 112B of rod 112, the plate 111B of the body 111 is provided with angular graduations 113 which, in the assembled condition of the tool 110, are centered on the axis Z112. In the exemplary embodiment considered here, as well visible in FIG. 3, the graduations 113 include seven main graduations, which are respectively associated with the markings <<−30>>, <<−20>>, <<−10>>, <<0>>, <<10>>, <<20>> and <<30>>, it being understood that too successive graduations around the axis Z112, from among these main graduations form between them an angle, centered on the axis Z112 and with a value of 10°. Further, always in the example considered here, and as well visible in FIG. 3, the graduations 113 include secondary graduations, which regularly subdivide the angular distance between the aforementioned main graduations and which are positioned on the border of the plate 111B, opposite to the rod 112.

As well visible in FIGS. 1 to 3, the plate 111B is also provided with through-holes 114 which each connect together the proximal and distal faces of the plate 111B, by extending parallel to the axis Z112 in the assembled condition of the tool 110. Each of the through-holes 114 is associated with at least some of the graduations 113, in this case, in the relevant example in the figures, with the aforementioned main graduations: in other words, in the assembled condition of the tool 110, each of the through-holes 114 occupy an angular position, around the axis Z112, identical with one of the aforementioned main graduations of the graduations 113, it being noted that for reasons which will appear later on, each of these main graduations is thus associated with two of the through-holes 114, one of these two through-holes being radially located far from the axis Z112 than the other one of these two through-holes.

Moreover, as illustrated in FIG. 1, the instrumentation 100 further comprises a bone attachment pin 120. The pin 120 is provided for crossing right through the plate 111B of the body 111, by being received complementarily in any of the through-holes 114.

Other features, in particular functional features, of the instrumentation 100 will be shown subsequently, within the scope of the use of this instrumentation for implanting, i.e. setting into place in a patient, a glenoidal prosthetic component 10 as shown in FIGS. 4 to 7.

The component 10 has two main opposite faces 10A and 10B, which, once the component 10 is implanted, correspond to respectively lateral and median faces in the anatomic sense of the term.

On its side face 10A, the component 10 is provided with a convex articular surface 11 which, in a way known per se and not detailed here, is intended to be jointed with a humeral prosthetic component, not shown in the figures. As shown in FIGS. 4 to 6, the articular surface 11 is for example of a spherical nature, corresponding to a sphere portion which is truncated by a geometrical plane at the median face 10B of the glenoidal component 10. According to this embodiment, the component 10 may be described as a glenosphere. This being the case, other convex geometries may be contemplated for the articular surface 11. In every case, this articular surface 11 defines a joint axis Z11, which extends between the side 10A and median 10B faces, while passing through the central region of the articular surface 11, and towards which is determined the articular cooperation between the glenoidal component 10 and the aforementioned humeral prosthetic component. For the example of the glenoidal component 10 considered in the figures, the joint axis Z11 passes through the geometrical centre of the spherical articular surface 11 and forms a central axis of symmetry for this surface 11.

As well visible in FIGS. 4 to 6, the articular surface 11 is provided, on its peripheral border, with a notch 11A made as a groove, which is not very deep and which extends in length parallel to the joint axis Z11. It is understood that this notch 11A gives the possibility of marking the angular position of the articular surface 11 and, as a consequence, the glenoidal component 10 around the joint axis Z11.

As visible in FIGS. 6 and 7, the glenoidal component 10 is moreover provided with a housing 12 which is recessed and set back from its median face 10B. This housing 12 is centered on an axis Z-Z, a so called implantation axis, and is peripherally delimited by a peripheral surface 12A which is frustoconical, while being centered on the implantation axis Z-Z, and being divergent towards the opening of the housing 12 on the median face 10B of the glenoidal component 10.

As well visible in FIGS. 5 to 7, the implantation axis Z-Z is parallel to the joint axis Z11, without however coinciding with this joint axis Z11. Thus, the implantation axis Z-Z is shifted relatively to the joint axis Z11. The result of this is that the housing 12 is eccentric relatively to the remainder of the glenoidal component 10, notably on the median face 10B of the latter, while being eccentric relatively to the joint axis Z11. In a projection in a plane perpendicular to the implantation axis Z-Z, as shown in FIGS. 5 and 7, the straight line, a so called eccentricity line, passing through the implantation axis Z-Z and through the joint axis Z11 is noted as EXC: as well visible in FIGS. 5 to 7, the notch 11A of the joint surface 11 is aligned with this eccentricity line EXC.

As shown in FIG. 4, the glenoidal component 10 is associated with a prosthetic plate 20, with which the glenoidal component 10 is designed so as to be fixedly assembled and which is itself provided so as to be anchored to the glenoid G of the scapula of a patient. The plate 20 includes a main body 21 which is dimensioned so as to be received complementarily and co-axially inside the housing 12: for this purpose, the main body 21 is centered on a geometrical axis which, in the assembled condition between the glenoidal component 10 and the plate 20, is aligned with the implantation axis Z-Z, and this main body 21 delimits, at its periphery, a frustoconical external surface 21A, which is centered on the aforementioned geometrical axis and which is complementary to the frustoconical peripheral surface 12A of the housing 12. The maximum radii of the surfaces 12A and 21A are substantially identical and their respective conicity angles are identical, which allows, by arranging the main body 21 of the plate 20 inside the housing 20 of the glenoidal component 10, of providing an adjusted surface support of the surfaces 12A and 21A against each other.

Thus, the assembly between the glenoidal component 10 and the plate 20, which results from the reception of the main body 21 inside the housing 12, is centered on the implantation axis Z-Z. This assembling is provided so as to be fixed, so as to immobilize the glenoidal component 10 and the plate 20 relatively to each other. Indeed, before its fixation of their assembly, the relative position of the glenoidal component 10 and of the plate 20 is adjustable around the implantation axis Z-Z, by rotation relatively to the main body 21 inside the housing 12 around the implantation axis Z-Z.

In practice, diverse embodiments may be contemplated as regards the fixation of the assembly between the glenoidal component 10 and the plate 20. A first fixation solution consists of jamming together the peripheral surface 12A of the housing 12 and the external surface 21A of the main body 21, by locking them with each other through a bond of the type <<Morse cone>>. Such jamming between the surfaces 12A and 21A is typically obtained by impaction of the glenoidal component 10 against the plate 20.

Another possibility for fixing the assembly between the glenoidal component 10 and the plate 20 lies in the use of a locking screw, such as the locking screw 30 contemplated for the exemplary embodiment considered in FIGS. 4 to 7, such a locking screw being described in detail in U.S. Pat. No. 6,969,406 to which the reader may refer for further details. Briefly, the locking screw 30 extends in the housing 12, as well as on either side of the latter, by being centered on the implantation axis Z-Z and it successively includes along this implantation axis Z-Z:

- a median terminal portion 30A produced as a finger with a smooth external surface, this finger being designed so as to be received in a central bore 22 of the plate 20, so as to center on the implantation axis Z-Z and to guide the reception of the main body 21 into the housing 12,
- an intermediate portion 30B, provided with threading which is provided for engaging a tapping complementary to the central bore 22, so as to allow screwing of the locking screw 30 into the plate 20, and
- a side terminal portion 30C, achieved as a head for driving the locking screw 30 in rotation on itself around the implantation axis Z-Z, this head being on the one hand designed for being engaged, via a passage 13 of the glenoidal component 10 which is centered on the implantation axis Z-Z and which opens onto the articular surface 11, by a maneuvering wrench, not shown and on the other hand supported by a dowel 40 with which is interiorly provided in a fixed way the glenoidal component 10.

As mentioned above, the plate 20 is intended to be anchored to a glenoid. In practice, the arrangements of the plate 20 allowing this anchoring are not limiting. In the exemplary embodiment considered in the figures, the main body 21 is for this purpose provided with through-holes 23, which connect to each other the lateral face of the main body 21, intended to be turned towards the glenoidal component 10 in the assembled condition of the latter with the plate, and the median face of this main body 21, opposite to its aforementioned side face: each of these through-holes 23 is designed for receiving a bone anchoring screw or a similar anchoring member, which is protracted through the main body 21 so as to press the median face of the main body 21 against the glenoid to which the plate 20 is to be anchored. Further, the main body 21 is securely provided with an anchoring pin 24, which extends, in a centered way on the implantation axis Z-Z, from the median face of the main body 21, the central bore 22 of the main body 21 being able to be extended inside this anchoring pin 24: the external surface of the anchoring pin 24 has raised/recessed portions, such as striations, which are able to retain the plate 20 relatively to the glenoid by cooperating, by fitting, with the walls of a cavity recessed in a suitable way in this glenoid.

As a non-limiting example, the glenoidal component 10 and the plate 20 belong to a shoulder prosthesis, such as the prostheses AEQUALIS REVERSED and AFFINITI marketed by TORNIER, Inc. and TORNIER SAS.

A method will now be described, notably with reference to FIGS. 8 to 16, for implanting the glenoidal component 10 on a glenoid G of a scapula S of a patient. In FIGS. 8 to 16, the relevant scapula S is the left scapula of the patient. As well visible in FIG. 8, the lower portion of the scapula S, laid out under the glenoid G, forms a pillar P.

This implantation method comprises two main, distinct and successive phases, i.e. a preoperative phase, which is applied before the surgical operation strictly speaking during which the soft tissues of the patient are incised in order to access to the glenoid G of his/her scapula S, and an intra-operative phase corresponding to the aforementioned surgical operation. Within the scope of this implantation method, the surgical instrumentation 100, described earlier with reference to FIGS. 1 to 3, is exclusively used during the intra-operative phase, as explained a little further on.

During the preoperative phase, the scapula S of the patient is observed in a non-invasive way in order to obtain preoperative data as to its geometry. In practice, these preoperative data stem from scanner images and/or radiological images of the scapula S. From these preoperative data, in particular on the basis of the scanner and/or radiological images, the implantation is simulated on the glenoid G of the glenoidal component 10 and of the plate 20: more specifically, the plot of the implantation axis Z-Z is contemplated, which induces a fixed geometrical positioning of the plate 20 on the glenoid G and consequently a geometrical positioning of the glenoidal component 10 relative to the glenoid G, this positioning of the glenoidal component 10 however not being fixed, but adjustable by simulation of the geometrical rotation of this glenoidal component 10 around the implantation axis Z-Z. This possible adjustment of the angular geometrical positioning of the glenoidal component 10 around the implantation axis Z-Z is utilized for determining an implantation angle α, with which the glenoidal component 10 is to be implanted relatively to the glenoid G so that, in a projection in a plane perpendicular to the implantation axis Z-Z, the eccentricity line EXC, which passes through the implantation axis Z-Z and the joint axis 11, avoids the pillar P of the scapula S. It will be noted that this preoperative determination of the implantation angle α is easy to carry out on the basis of scanner and/or radiological images, taken in geometrical planes perpendicular to the implantation axis, such images giving the possibility of viewing the tilt to be selected for the eccentricity line EXC in order that it avoids the pillar P, i.e. in order that it does not intersect this pillar P.

The implantation angle α, which is thus determined during the preoperative phase, is measured relatively to anatomic marks of the glenoid G. According to a practical embodiment, this implantation angle α is obtained by measuring in a projection in a plane perpendicular to the implantation axis Z-Z, the geometrical angle formed between the eccentricity line EXC and a reference line REF which is straight and which passes through the implantation axis Z-Z and the anatomic apex, i.e. the uppermost bone point of the glenoid G. This being the case, other anatomic marks of the glenoid G may be contemplated for allowing quantification of the implantation angle α, determined during the preoperative phase.

Figure 8:
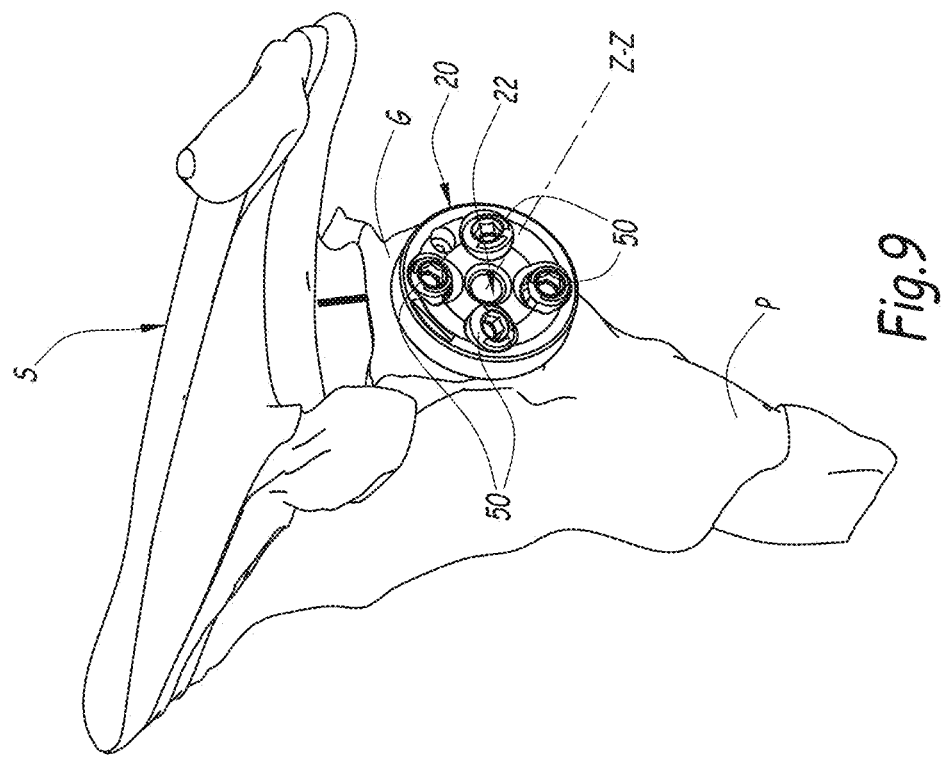
FIG. 8, FIG. 9, FIGS. 10 and 11, FIG. 12, FIG. 13, FIG. 14, and FIGS. 15 and 16 respectively illustrate successive steps of the implantation of the prosthetic set of FIG. 4 on a glenoid of a patient, FIGS. 8, 9, 10, 12, 14 and 15 being perspective views while the FIGS. 11 and 16 are elevational views according to the arrow XI of FIG. 10 and the arrow XVI of FIG. 15 respectively, FIG. 13 being an elevational view similar to FIGS. 11 and 16.

During the intra-operative phase, the glenoid G of the scapula S is accessed after having cut the soft tissues which surround this glenoid G. The glenoid G is then prepared with view to receiving the plate 20. To do this, in a way known per se and as illustrated in FIG. 8, the glenoid G is milled or more generally prepared by means of suitable cutting tools. This preparation of the glenoid G also provides localization of the anatomic mark(s), which have been selected during the preoperative phase for measuring the implantation angle α. In the example considered here, the apex of the glenoid G is thus localized, i.e. its upper bone point GA, as shown in FIG. 8.

If need be, after having localized the upper bone point GA of the glenoid G, this upper point GA is materialized by a physical marking of the glenoid G, for example in the form of a notch in the bone material, made with the electric scalpel, as indicated schematically by a thickened segment in FIG. 8 and the following figures. In this way, the subsequent viewing of the upper bone point GA of the glenoid G is facilitated during the intra-operative phase.

Within the scope of the preparation of the glenoid G with view to laying the plate 20 of FIG. 4, a cavity C is dug in the glenoid G, which is intended to receive the anchoring pin 24 and which, consequently, is centered on an axis materializing the implantation axis Z-Z. As a non-limiting example, the central axis of the cavity C is provided perpendicular to the milling plane of the glenoid G and is provided for passing through the intersection between the straight line, connecting the upper GA and lower GB bone points together of the glenoid G, and the straight line, connecting the anterior GC and posterior GD bone points together of the glenoid. Of course, other possibilities may be contemplated for localizing and tilting the implantation axis Z-Z relatively to the glenoid G, from the moment that the materialization of this implantation axis Z-Z observes the planning which has been made thereof in the preoperative phase. In particular, at the end of this step for preparing the glenoid G, the straight line which, in projection in a plane perpendicular to the implantation axis Z-Z, passes through the implantation axis and the upper bone point GA of the glenoid G, corresponds to the reference line REF which had been planned during the preoperative phase.

Figure 9:
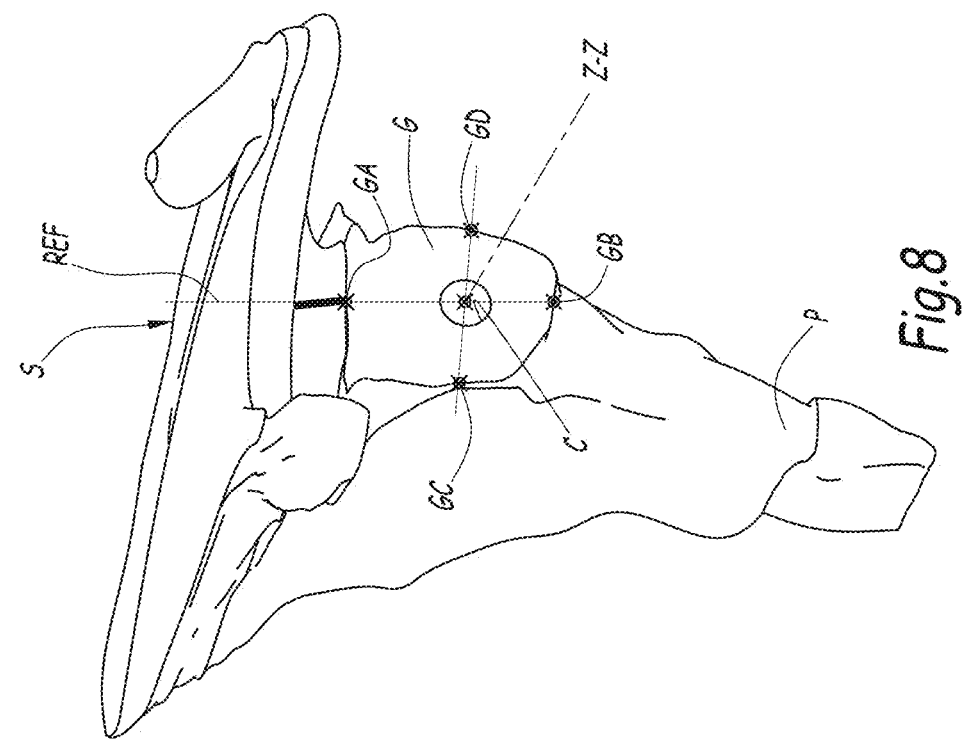

The intra-operative phase continues by the laying of the plate 20 on the glenoid G, as illustrated with FIG. 9. In particular, the anchoring pin 24 of this plate is fitted into the cavity C and screws 50 are added in the holes 23 of the plate so as to be anchored in the glenoid G. The plate 20 is thus anchored to the glenoid G.

Figure 11:
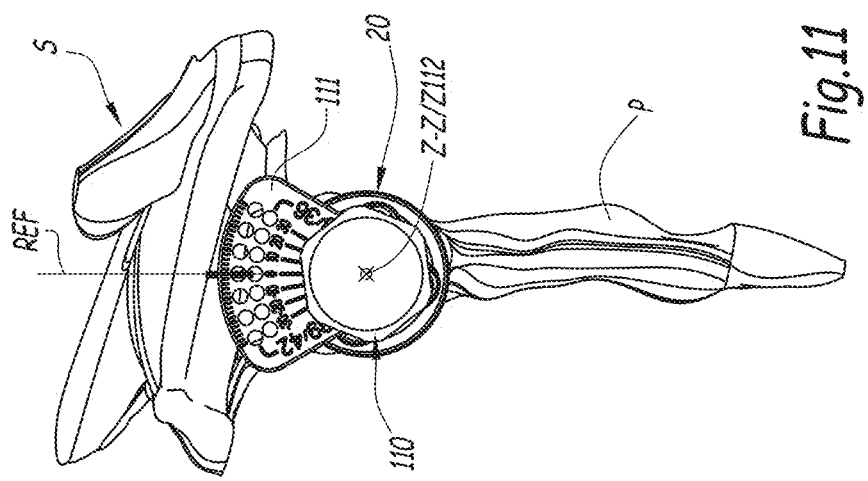
Figure 10:
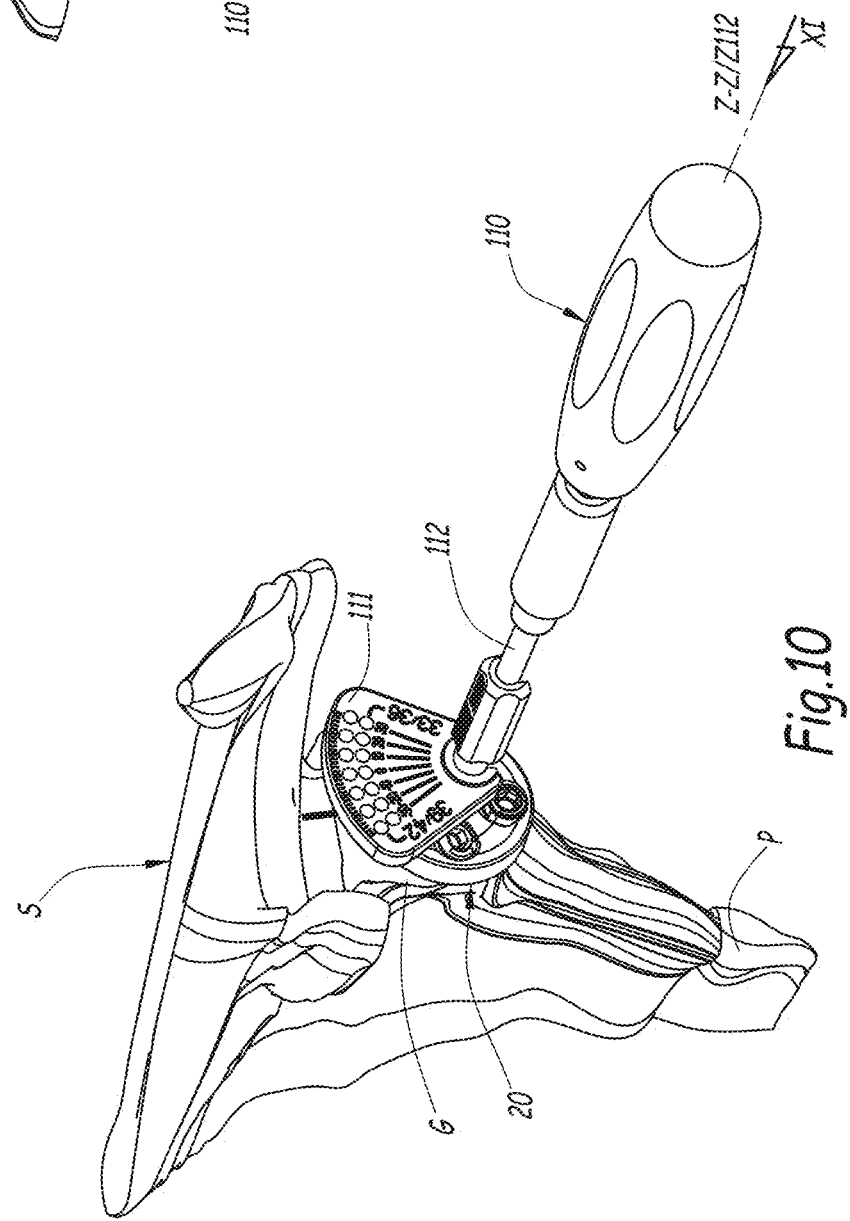

The intra-operative phase then continues by using the instrumentation 100 tool 110, as illustrated in FIGS. 10 and 11. Thus, the distal terminal portion 112A of the rod 112 of the tool 110 is introduced into the central bore 22 of the plate 20 so as to align the axis Z112 and the implantation axis Z-Z. To do this, a practical embodiment consists of providing that the distal terminal portion 112A of the rod 112 cooperates by shape matching with the central bore 22 of the plate 20, it being understood that, as an alternative not shown, other possibilities for cooperation may be contemplated between the distal terminal portion 112A of the rod 112 and the plate 20. In every case, the rod 112 is found centered on the implantation axis Z-Z, as this is well visible in FIG. 11.

The angular position of the body 111 of the tool 110, around the implantation axis Z-Z, is then adjusted so that, as well visible in FIG. 11, its graduation "0" is aligned with the upper bone point GA of the glenoid G. More generally, it is understood that in this step, a matching is established between the angular positioning of the body 111 around the implantation axis Z-Z and the aforementioned reference line REF. In practice, the adjustment of the angular position of the body 111 is achieved by rotary swinging of the gun 111A around the running portion 112C of the rod 112.

Figure 12:
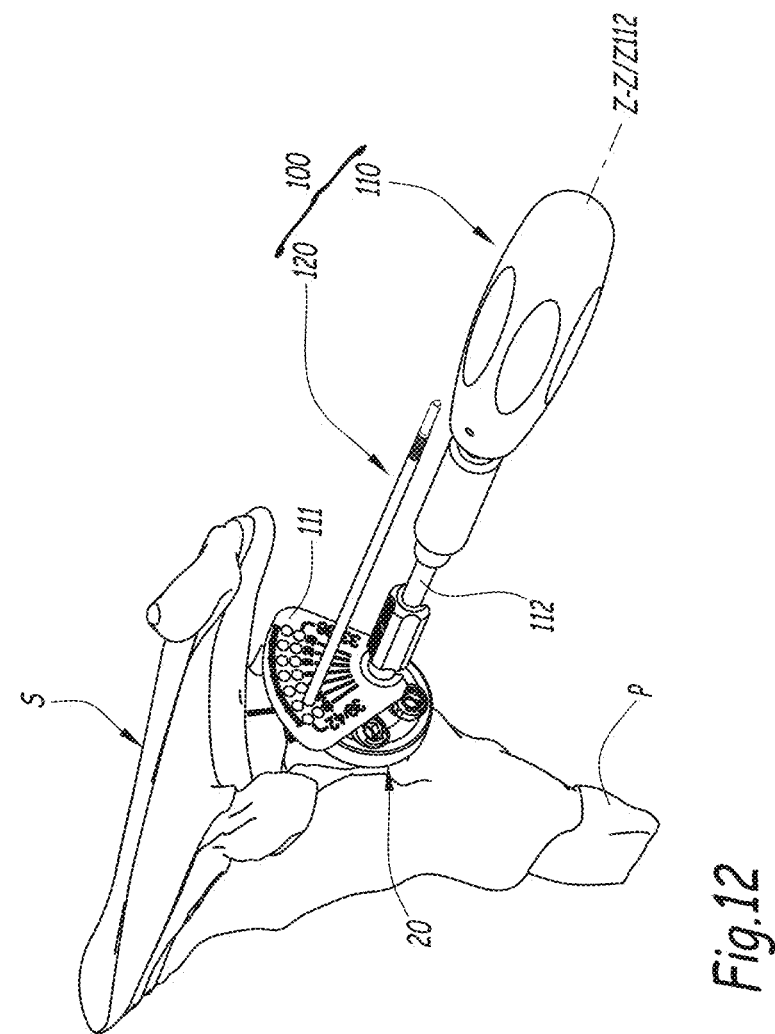

Without modifying the position of the tool 110 relatively to the glenoid G, the pin 120 is then used, as shown in FIG. 12. This pin 120 is introduced into one of the through-holes 114 of the tool 110. The hole 114 receiving the pin 120 is associated with the main graduation, from among the graduations 113, the closest to the implantation angle α determined during the preoperative phase. In the relevant example here, the relevant through-hole 114 is associated with the main graduation "−20".

Optionally, before setting into place the pin 120 on the glenoid G, another pin, similar to this pin 120 but distinct from the latter, may be set into place on the glenoid G, by being introduced through the through-hole 114 associated with the graduation "0": in this way, the angular position of the body 111 around the axis Z112 of the rod 112 is immobilized relatively to the glenoid G, in particular during the setting into place of the pin 120.

Figure 13:
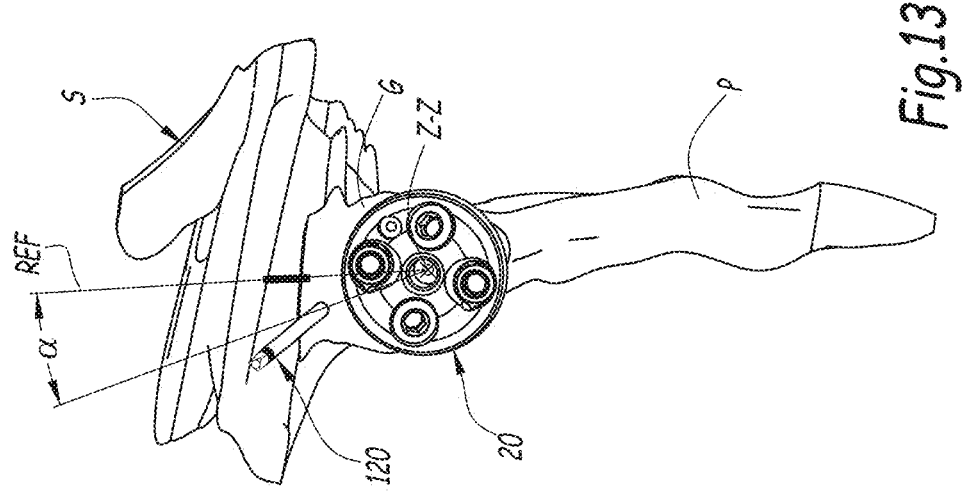

The tool 110 is then disengaged, while maintaining in place the pin 120 on the glenoid G, as illustrated with FIG. 13: it is understood that the pin 120, the setting into place of which has been guided by the tool 110, localizes the implantation angle α. In other words, the tool 110 gives the possibility, during the intra-operative phase, of only protracting relatively to the glenoid G the implantation angle α, giving the possibility of building this implantation angle α relatively to an anatomic mark which is planned during the preoperative phase, such as the upper point GA of the glenoid G.

Figure 14:
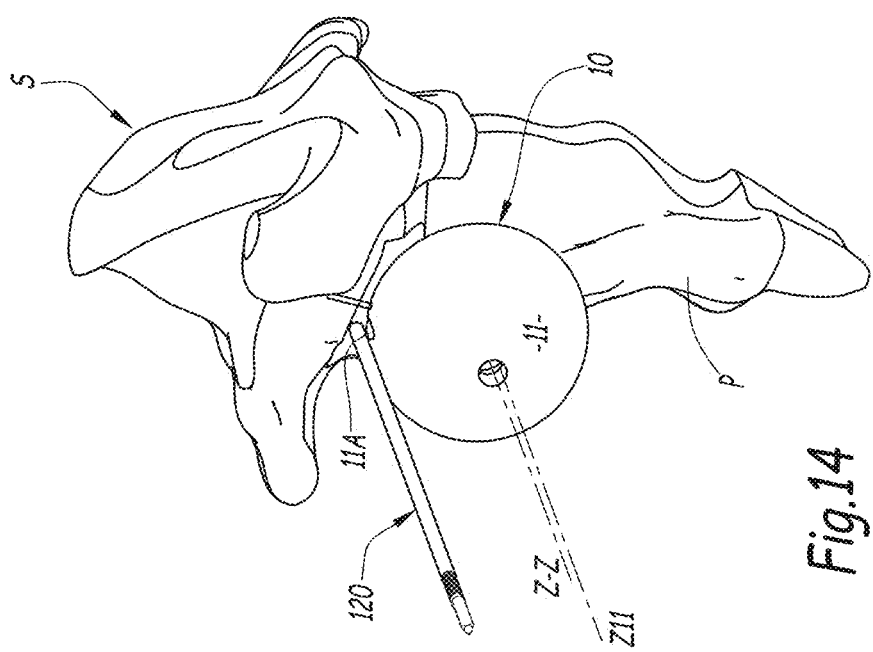

The glenoidal component 10 is then assembled to the plate 20, as shown in FIG. 14. As explained above, the housing 12 of the glenoidal component 10 then receives the main body 21 of the plate 20.

Figure 15:
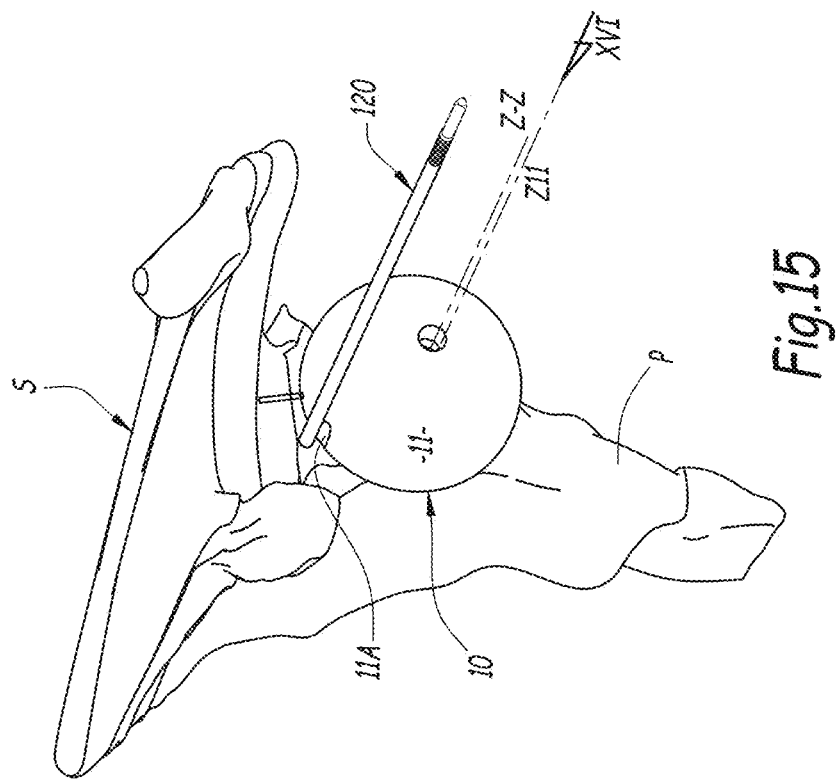
Figure 16:
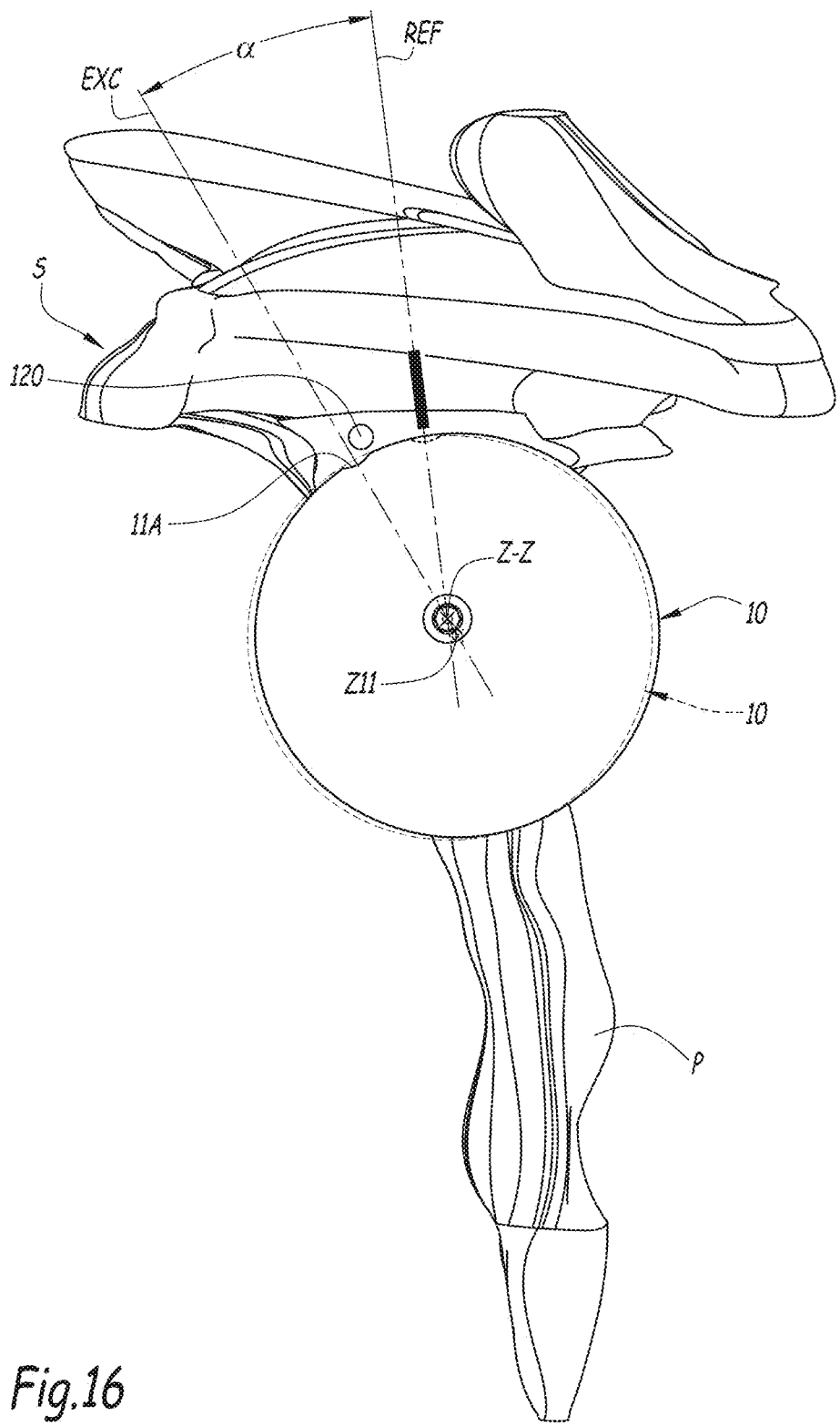

Before fixing the assembly between the glenoidal component 10 and the plate 20, the angular position, around the implantation axis Z-Z of the glenoidal component 10 relatively to the plate 20 is adjusted, as shown by comparison between FIGS. 14 and 15. Thus, while being assembled to the plate 20, the glenoidal component 10 is swung along the implantation axis Z-Z, until the notch 11A of its articular surface 11 is aligned with the pin 120 maintained in place on the glenoid G. The glenoidal component 10 then occupies the position which is illustrated with FIG. 15 and which is drawn in solid lines in FIG. 16: in this position of the glenoidal component 10, the angle which, in projection in a plane perpendicular to the axis Z-Z, is formed between the reference line REF and the eccentricity line EXC, actually corresponds to the implantation angle α. The assembly between the glenoidal component 10 and the plate 20 may then be fixed, thereby observing the implantation angle α which had been determined during the preoperative phase. FIG. 16 gives the possibility of appreciating that the eccentricity line EXC, which as explained above, passes both through the notch 11A, the implantation axis Z-Z and the joint axis Z11, actually avoids the pillar P of the scapula S, as planned during the preoperative phase. Conversely, it will be noted that if the glenoidal component 10 had been implanted by positioning its notch 11A in alignment with the upper bone point GA of the glenoid G, as this is indicated in dotted lines in FIG. 16, the geometrical straight line, which in projection in a plane perpendicular to the Z-Z axis, would pass through this implantation axis Z-Z and the joint axis Z11, would intersect the pillar P.

In order to facilitate the observation of the alignment of the pin 120 with the notch 11A, it is understood that it is preferable that this pin 120 be located in close proximity to the peripheral edge of the articular surface 11. Also, the through-holes 114 of the tool 110 are advantageously positioned at a radial distance relatively to the axis Z112 of the rod 112, which is provided to be slightly greater than the radius of the peripheral edge of the articular surface 11. The foregoing consideration also gives the possibility of understanding the benefit of distributing the through-holes 114 in two series, within each of which, the holes 114 are located at a same radial distance from the axis Z112, the respective radial distances of both of these series being different from each other, like for the embodiment considered in the figures: indeed, each series of through-holes 114 may thus be associated with a corresponding size for the glenoidal component 10, characterized by the radius or the diameter of the peripheral edge of the articular surface 11 of this glenoidal component 10.

Diverse layouts and alternatives to the instrumentation 100 described up to now, as well as the use of this instrumentation, may be contemplated.

Thus, in FIGS. 17 and 18, an optional layout of the tool 110 consists of adding to the tool considered in FIGS. 1 to 3, a sight 115. This sight is provided to the movable relatively to the body 111 so as to individually aim at each of the graduations 113. In practice, the sight 115 is for example mounted so as to freely rotate on the gun 111A of the body 111, around the axis Z112 of the rod 112. In every case, this sight facilitates the localization of the graduations 113.

Moreover, in addition to being able to be used in association with the pin 120 for protracting the implantation angle α by localizing the latter with this pin, the tool 110 may be used as an instrument for measuring the relative angular position of the glenoidal component 10 relatively to the plate 20 around the implantation axis Z-Z. This measurement made by the tool 110 may be conducted as a verification at the end of the implantation of the glenoidal component 10. This measurement may also be applied before fixation of the assembly between the glenoidal component 10 and the plate 20, and this alternatively to the use of the pin 120: indeed, during the intra-operative phase, before assembling between the glenoidal component 10 and the plate 20, the angular positioning of the glenoidal component 10 relatively to the plate 20 may be adjusted by trial and error, while regularly measuring, with the tool 110, the angle formed between the eccentricity line EXC and the reference line REF, and this until this angle is substantially equal to the implantation angle α determined during the preoperative phase. The use of the sight 115 facilitates such a use of the tool 110 as a measurement instrument. In every case, it is understood that the tool 110 is thus used while the glenoidal component 10 is already assembled to the plate 20, which is made possible by the introduction of the distal terminal portion 112A of the rod 112 through the passage 13 of the glenoidal component 10, the free end of this distal terminal portion 112A will then cooperate either directly with the main bore 22 of the plate 20, or with the imprint delimited by the side terminal portion 30C of the locking screw 30.

Another possibility of use of the tool 110 may be applied before setting into place the plate 20 on the glenoid G. Indeed, as explained above, the preparation of the glenoid G during the intra-operative phase may lead to having a materialization of the implantation axis Z-Z even before implanting the plate 20: in the example considered above, the central axis of the cavity C dug in the glenoid materializes the implantation axis Z-Z, as shown in FIG. 8. Consequently, by introducing and centering the distal terminal portion 112A of the rod 112 in the cavity C before setting into place the plate 20, the instrumentation 100 may be used for protracting the implantation angle α relatively to the glenoid G, as described earlier; in particular, the tool 110 is used for building the implantation angle α relatively to an anatomic marking. Once the tool 110 is cleared, the plate 20 and the glenoidal component 10 are set into place without using the tool 110 again, the angular positioning of the glenoidal component 10 being then adjusted so as to observe the implantation angle α before fixing their assembly.

As alternatives not shown, embodiments other than the graduations 113 may be contemplated as localization elements, fixedly provided on the body 111 of the tool 110, in order to localize the implantation angle α.

The invention claimed is:

1. Instrumentation for implanting a glenoidal prosthetic component on a glenoid of a patient,
   the glenoidal prosthetic component being provided with a convex articular surface which defines a joint axis and which is intended to articulate with a humeral prosthetic component,
   the glenoidal prosthetic component being also adapted to be fixedly assembled with a plate to be anchored to the glenoid, an assembly between the glenoidal prosthetic component and the plate being centered on an implantation axis which is both parallel and shifted with respect to the joint axis, the glenoidal prosthetic component being rotatable around the implantation axis with respect to the plate before fixing the assembly,
   wherein the instrumentation comprises a tool for positioning the glenoidal prosthetic component and the plate relatively to each other, rotatably around the implantation axis,
   wherein the tool is configured to intra-operatively protract an implantation angle with respect to the glenoid, wherein the implantation angle is in a plane transverse to the implantation axis and is centered on the implantation axis, the tool comprising a body, which, in use, extends transversely to the implantation axis and which is provided with localization elements for localizing the implantation angle, the localization elements comprising visible graduation markings disposed on a proximal face of the body in an array indicating a plurality of spaced apart and progressively larger non-zero angles which are in said plane and are centered on the implantation axis.

2. The instrumentation according to claim 1, wherein the tool further comprises an elongated rod which is centered on a geometrical axis that, in use, aligns with the implantation axis, and wherein the elongated rod comprises a distal end part, a proximal end part, and a running portion, which connects the distal end part and the proximal end part, wherein the running portion bears the body.

3. The instrumentation according to claim 2, wherein the distal end part of the elongated rod is adapted for cooperating with the plate so as to center the elongated rod on the implantation axis.

4. The instrumentation according to claim 3, wherein the distal end part of the elongated rod is adapted for cooperating by shape matching with the plate so as to center the elongated rod on the implantation axis.

5. The instrumentation according to claim 3, wherein the proximal end part of the elongated rod is provided with a handle.

6. The instrumentation according to claim 1, wherein the tool further comprises a sight which is movable with respect to the body so as to individually aim at each of the localization elements.

7. The instrumentation according to claim 1, wherein the instrumentation further comprises at least one pin able to be attached to the glenoid, and wherein the tool is adapted for guiding and setting into place said at least one pin on the glenoid so that said at least one pin localizes the implantation angle.

8. The instrumentation according to claim 7, wherein the body is provided with through-orifices which are associated with at least some of the localization elements and which are each adapted for receiving in a complementary way said at least one pin so as to guide and set into place said at least one pin on the glenoid.

* * * * *